United States Patent [19]
Gray et al.

[11] Patent Number: 5,456,859
[45] Date of Patent: Oct. 10, 1995

[54] LIQUID CRYSTAL CYANOALKANES AND CYANOALKENES

[75] Inventors: George W. Gray, Wimborne; David Lacey; Kenneth J. Toyne, both of Hull, all of England; Ibraham G. Shenouda, Kent, Ohio; Abdul Luheshi, Braintree, England

[73] Assignee: The Secretary of State for Defence in Her Britannic Majesty's Government of the United Kingdom of Great Britain and Northern Ireland, London, England

[21] Appl. No.: 958,061

[22] Filed: Oct. 8, 1992

[30] Foreign Application Priority Data

Feb. 8, 1990 [GB] United Kingdom ............ 9002830

[51] Int. Cl.[6] ............ C09K 19/30; C09K 19/12; C07C 255/00; G02F 1/13
[52] U.S. Cl. ............ 252/299.63; 252/299.66; 252/299.01; 558/388; 359/103
[58] Field of Search ............ 252/299.63, 299.66, 252/299.65, 299.6, 299.01; 558/388, 389, 406; 359/103

[56] References Cited

U.S. PATENT DOCUMENTS

| | | | |
|---|---|---|---|
| 4,622,163 | 11/1986 | Huynh-Ba et al. | 252/299.61 |
| 5,002,694 | 3/1991 | Wachtler et al. | 252/299.61 |
| 5,133,896 | 7/1992 | Coates et al. | 252/299.65 |
| 5,173,211 | 12/1992 | Yamashita et al. | 252/299.61 |
| 5,183,586 | 2/1993 | Terada et al. | 252/299.61 |
| 5,186,858 | 2/1993 | Terada et al. | 252/299.61 |
| 5,230,830 | 7/1993 | Coates et al. | 252/299.67 |
| 5,232,625 | 8/1993 | Gray et al. | 252/299.63 |
| 5,252,252 | 10/1993 | Huynh-Ba et al. | 252/299.6 |
| 5,364,559 | 11/1994 | Shinjo et al. | 252/299.6 |

FOREIGN PATENT DOCUMENTS

| | | |
|---|---|---|
| 0134750 | 3/1985 | European Pat. Off. . |
| 0158252 | 10/1985 | European Pat. Off. . |
| 254590 | 3/1988 | Germany . |
| 3731619 | 4/1988 | Germany . |
| 585703 | 3/1977 | Switzerland . |

*Primary Examiner*—Cynthia Harris
*Attorney, Agent, or Firm*—Nixon & Vanderhye

[57] ABSTRACT

There is disclosed a cyanoalkane and cyanoalkene of general formula (I) which shows liquid crystalline properties: wherein R and $R^1$ are independently $C_{1-12}$ alkyl, alkoxy, perfluoroalkyl or perfluoroalkoxy; rings A, B, C and D are independently phenyl, which may carry one or two halogen substituents, trans-cyclohexyl, or (2, 2, 2) bicyclooctyl, each of a, b, c or d being independently 0 or 1 provided (a+b+c+d) is 2 or 3; links A and C are independently a single bond, $CH_2CH_2$, COO, OOC, $CH_2O$ or $OCH_2$; n, m and p are independently 0 or an integer 1 to 4 provided (n+m+p) is not 0; W and Z are independently selected —CH=C(CN)— and —C(CN)=CH—; X and Y are independently selected from —CHCN— and —C(CN)$_2$—; w, x, y and z are 0 or 1, provided that w and z are 0 if x and/or y are 1, and further provided that at least one of w, x, y and z is 1.

36 Claims, 6 Drawing Sheets

Route A

Ts = toluene - 4 - sulphonate

Fig. 1.
Route A
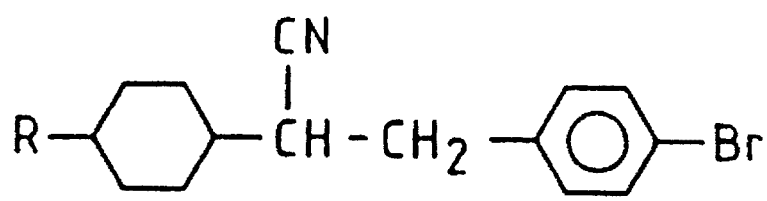
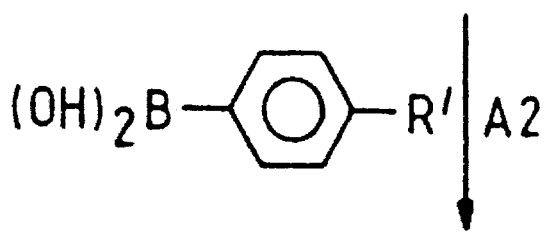
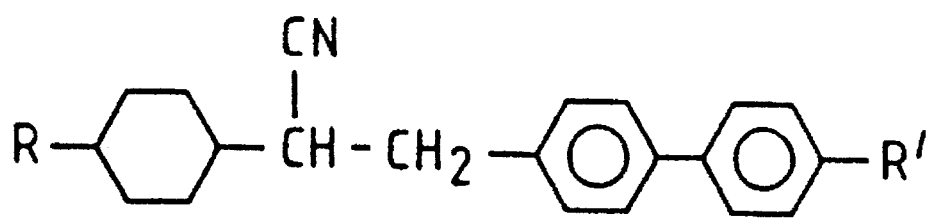
Ts = toluene − 4 − sulphonate

Fig. 2.
Route B
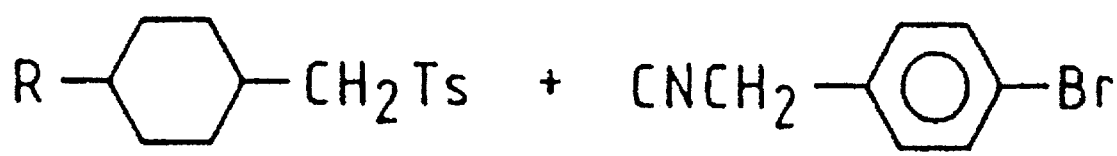
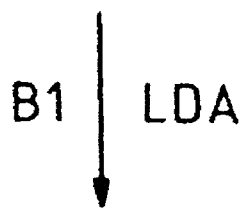
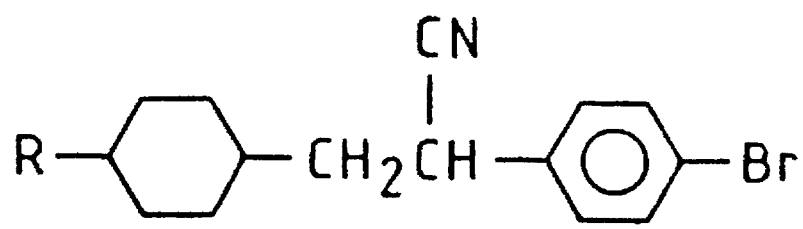
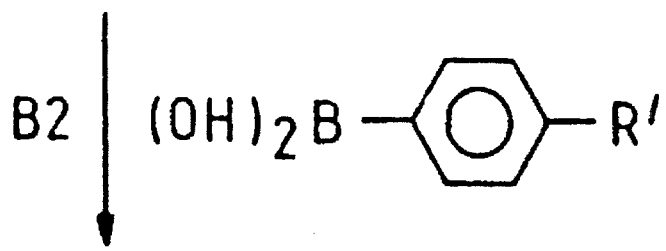
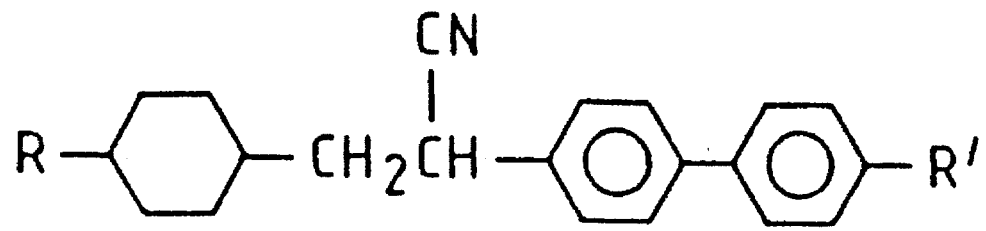

Fig. 4.  Route D

Fig. 5. Route G

R, R" = alkyl
one of a and b = 1 the other = 0

LIQUID CRYSTAL CYANOALKANES AND CYANOALKENES

This invention relates to cyanoalkanes and cyanoalkenes which show liquid crystalline properties, and to liquid crystal materials and devices which incorporate them.

BACKGROUND OF THE INVENTION

Liquid crystal materials and devices are well known, and generally exploit the useful hemeric (N) and smectic (S), especially smectic C and I (Sc, SI) liquid crystal phases, which show electro-optical characteristics. The Sc phase shows its most useful characteristics when an optically active compound is present in the material, forming a ferroelectric chiral smectic C (Sc) phase.

Liquid crystal materials are generally mixtures of compounds, and desirable requirements for such a mixture and/or its constituent compounds include ease of preparation and liquid crystal phases of a useful type which persist over a broad temperature range preferably including room temperature. Other desirable requirements may be sought for particular applications, for example a useful birefringence, dielectric anisotropy, a useful phase transition sequence such as Sc-SA with increasing temperature, and in the case of Sc materials, the ability to form a mixture with a high spontaneous polarisation (Ps).

A wide variety of compounds which show liquid crystal phases are known, for example:

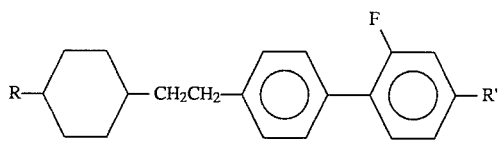

compounds where R and R' are alkyl, disclosed in EP-A-0,117,631. Another useful structural type for example is:

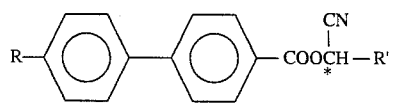

where R and R' are alkyl, disclosed in PCT/GB87/00441.

It is widely acknowledged that minor structural variations in liquid crystal compounds can have a drastic and unexpected effect on their liquid crystalline properties. It is therefore an object of this invention to explore novel structural types and identify those which show liquid crystal phases, especially of a useful type.

SUMMARY OF THE INVENTION

According to this invention, novel cyanoalkanes and alkenes are provided, of general formula I:

rings A, B, C and D are independently phenyl, which may carry one or two halogen substituents, transcyclohexyl or (2,2,2) bicyclooctyl, each of a, b, c or d being independently 0 or 1 provided (a+b+c+d) is 2 or 3;

links A and C are independently a single bond, $CH_2CH_2$, COO, OOC, $CH_2O$ or $OCH_2$;

n, m and p are independently 0 or an integer 1 to 4 provided (n+m+p) is not 0;

W and Z are independently selected from —CH=C(CN)— and —C(CN)=CH—;

X and Y are independently selected from —CHCN— and —C(CN)$_2$—;

w, x, y and z are 0 or 1, provided that w and z are 0 if x and/or y are 1, and further provided that at least one of w, x, y and z is 1.

BRIEF DESCRIPTION OF THE DRAWINGS

FIGS. 1–5 are synthetic schemes for synthetic routes A, B, C and G, respectively.

DETAILED DESCRIPTION OF THE INVENTION

Figure 3:
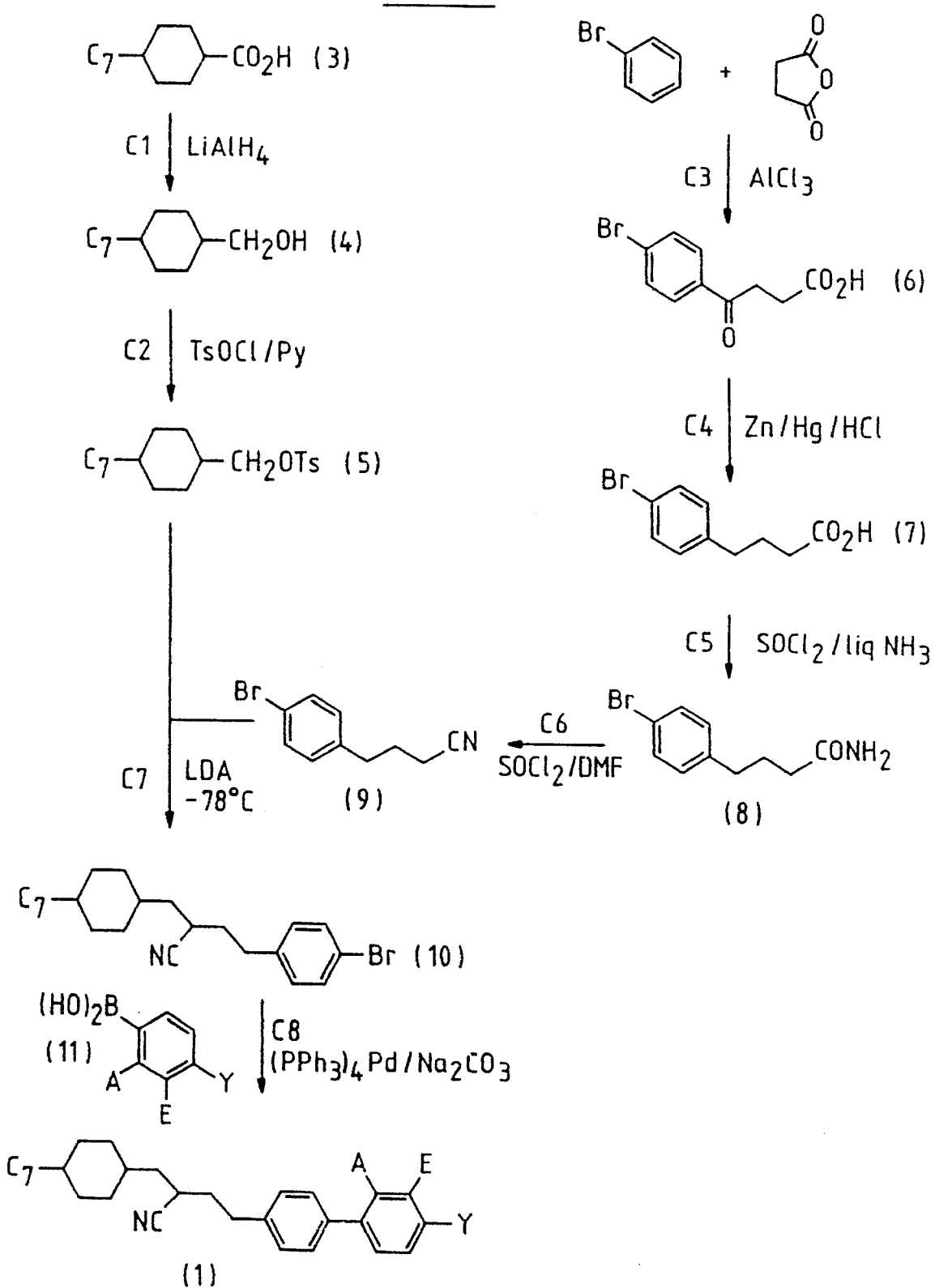
Figure 4:
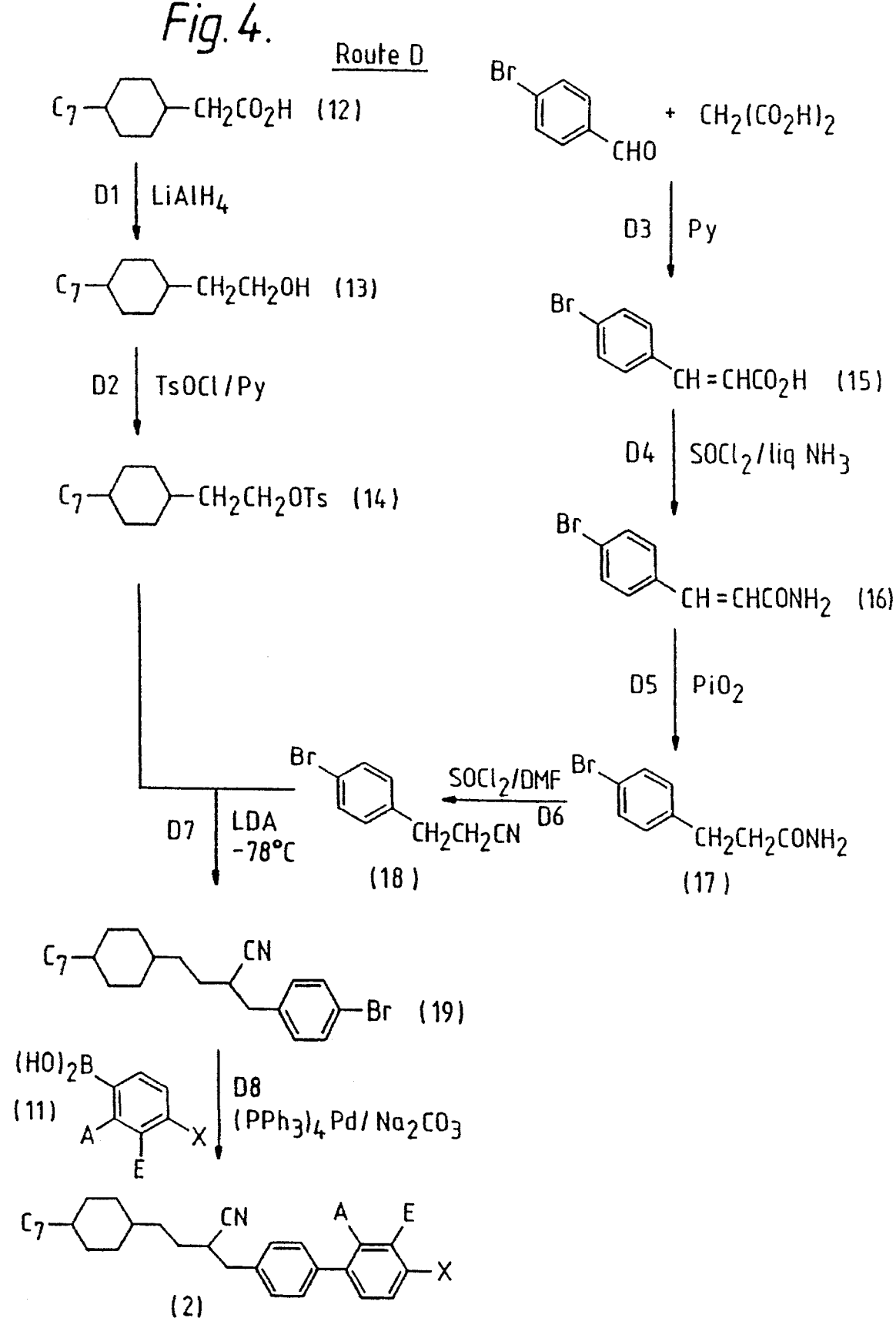
Figure 5:
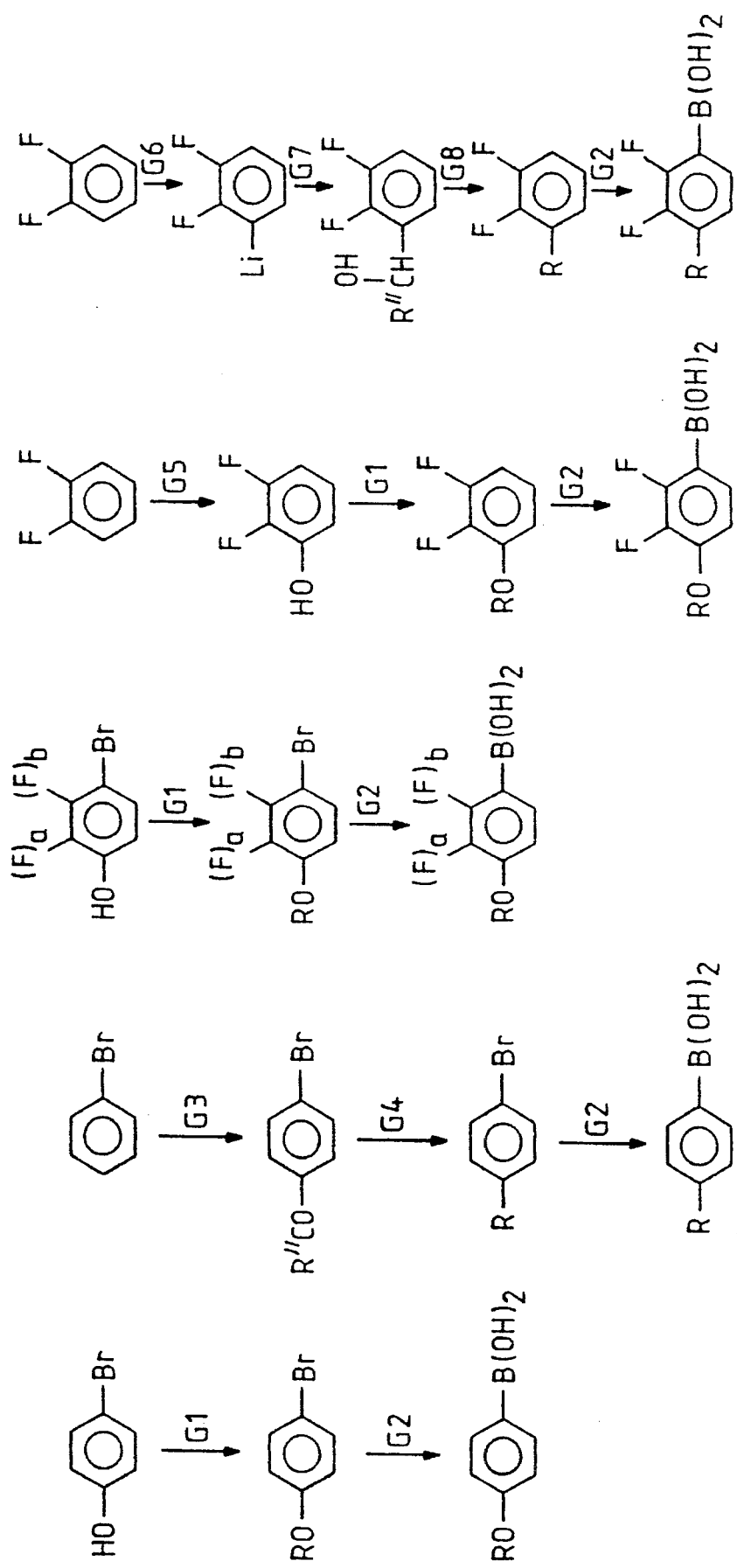

In the above structural formula, there are several preferred subgroups and substituents.

R and R' may be straight chain or branched chain, including asymmetrically substituted chains. When rings A, B, C or D carry substituents these may be in any of the available substitution positions. When a unit —CHCN— is present it may be asymmetrically substituted or a racemane.

The structural preferences discussed below are inter-alia on the basis of ease of preparation and/or usefulness in liquid crystal materials.

Preferably R and R' are independently n-alkyl or n-alkoxy, or asymmetrically substituted alkyl or alkoxy. Preferably rings A and B are cyclohexyl. Preferably if rings C and D are halogen substituted phenyl the halogen is fluorine. Preferably the links A and C are single bonds. Preferably if c and d are 0, R' is alkyl. Preferably only ring A is (2,2,2) bicyclooctyl.

Some preferred combinations of the variables relating to the cyanoalkane or cyanoalkene bridge between rings B and C shown in formula I are:

(A) n, w, y, z, p=0; x, m=1; X=CHCN (B) w, m, y, z, p=0; n, x=1: X=CHCN (C) w, m, y, z, p=0; n, x=1, X=C(CN)$_2$ (D) n, x, m, y, z, p=0; w=1; W=—CH=C(CN)—

(E) w, y, z, p=0; x, m=1; n=2; X=CHCN or C(CN)$_2$ (F) n, w, z, p=0; x, y=1; m=4; X, Y=CHCN

Specific examples of structures embodying these combinations are listed below in table 1 wherein the capital letter indicates the combination represented.

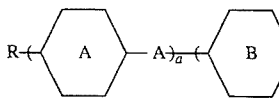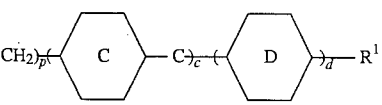

Formula I wherein R and R' are independently $C_1$–$C_{12}$ alkyl, alkoxy, perfluoroalkyl or perfluoroalkoxy;

TABLE 1

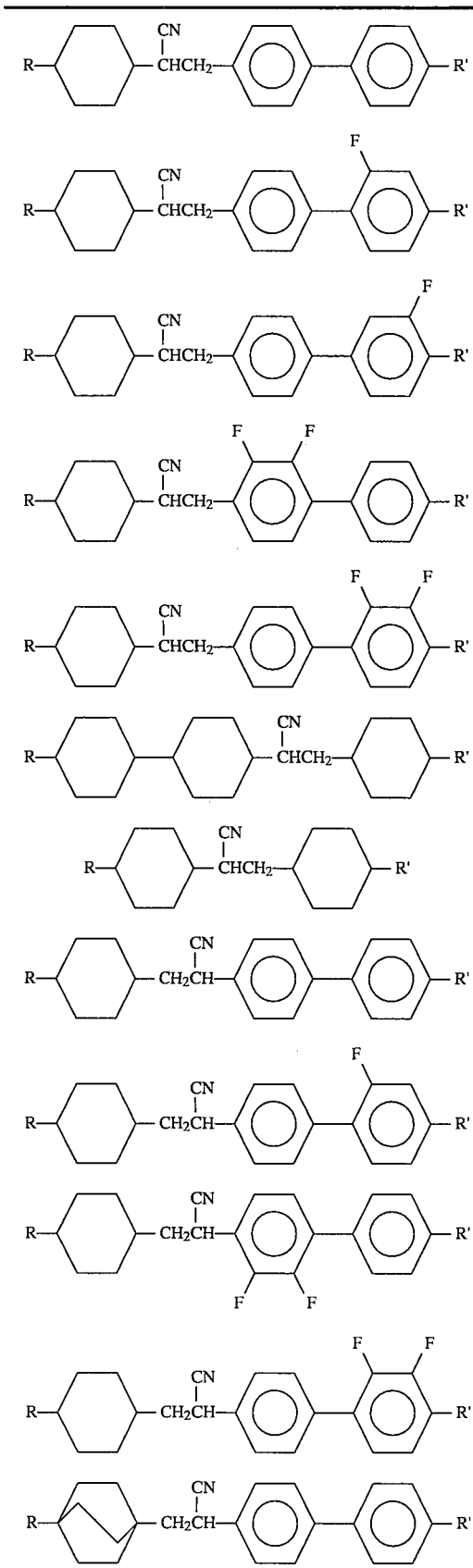

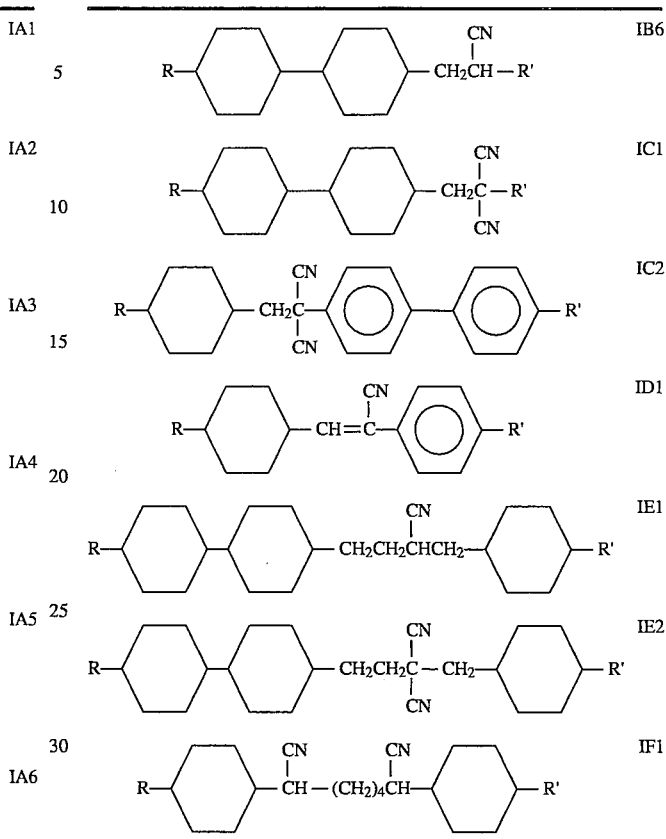

Of these formulae, IA1, IA4, IA5, IB2, IB3 and IB4 are particularly preferred.

Compounds of formula I, for example those listed in Table 1, may be prepared by a number of preparative routes starting from known compounds, or by variants of these which will be apparent to a skilled chemist. General routes A and B to compounds IA and IB are shown schematically in the accompanying figures.

Steps A1 and B1 use lithiumdiisopropylamide (LDA) as a coupling reagent, and steps A2 and B2 involve coupling of the brominated product with a phenyl boronic acid. Methods for preparation of phenylboronic acids are well known, for example, reaction of a starting phenyl with tri-isopropylborate. By using an appropriately substituted starting phenyl, e.g. a 2- or 3-fluoro, or 2, 3-difluoro alkyl or alkoxy phenyl, the corresponding 4-phenyl boronic acid may be prepared.

Methods for preparation of such phenylboronic acids are shown in route G.

In route G the steps are as follows:

G1: 1-bromoalkane, $K_2CO_3$, acetone, reflux

G2: react with n-butyllithium, then tri-isopropylborate at −78° C.

G3: Friedel Crafts addition

G4: Reduction, e.g. using hydrazine hydrate

G5: See M. F. Hawthorne, J. Org. Chem. (1957), 22, 1001

G6: n-butyllithium

G7: R-CHO

G8: (i) $P_2O_5$, (ii) Pd/C, $H_2$

Examples of the use of route G to prepare phenyl boronic acids are described in GB-A-8806220 and PCT/EP88/

00724, the contents of which are included by reference.

Hence routes A and B are of general applicability and although illustrated for specific structures it will be apparent to those skilled in the art how they can be adapted to produce other structural types.

Compounds of structural types C, D and E, e.g. IC, ID and IF may be prepared by reaction of the corresponding Ketone with trimethylsilylcyanide (TMS-CN) after reaction of the Ketone with titanium tetrachloride. Many suitable Ketones are known, but synthetic routes to Ketones are so well known, e.g. Friedel Crafts type additions using acyl chlorides or reaction of nitriles with Grignard reagents that if commercially unavailable they may be synthesised.

Compounds of formula I may be mixed with known liquid crystalline compounds to form useful liquid crystal materials. This invention therefore also provides a liquid crystal material, being a mixture of compounds at least one of which is a compound of formula I. In this aspect of the invention, compounds of structural types A and B e.g. IA and IB are preferred as constituents of smectic C liquid crystal materials, in view of the fact that they show Sc phases, have a negative dielectric anisotropy ($\Delta\epsilon$) and a low birefringence ($\Delta\eta$).

Compounds of formula I, e.g. of structural types A and B, especially IA and IB may be used in Sc mixtures together with known compounds with either together or separately form an Sc phase, particularly preferred compounds of this type being those of formulae IIA and IIB below:

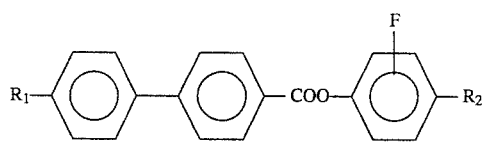
IIA

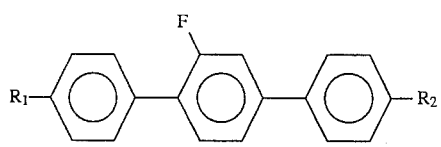
IIB1

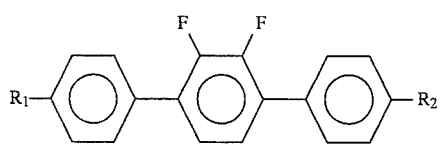
IIB2

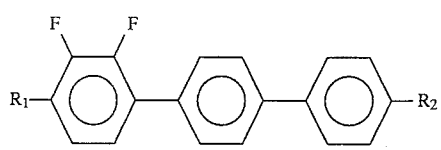
IIB3 wherein $R_1$ and $R_2$ are independently $C_2-C_{12}$ alkyl or alkoxy.

If the compound(s) of formula I present in the Sc mixture contains an asymmetrically substituted group, for example if R, R' or —CH(CN)— is asymmetrically substituted, then the Sc phase may be a ferroelectric Sc phase. Alternately or additionally the mixture may contain known asymmetrically substituted compounds which are capable of inducing Sc phases to be Sc phases. Many such compounds are known, but preferred compounds are those described in PCT/GB87/00441, especially those of formula III

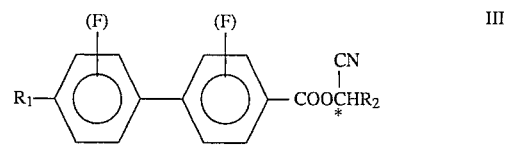
III where (F) indicates that the ring indicated may carry a lateral fluorine substituent and $R_1$ may be $C_{1-12}$ n-alkyl or n-alkoxy and $R_2$ may be $C_{1-15}$ alkyl, or n-alkyl or a branched chain or optically active alkyl.

Typically but not exclusively and Sc mixture of this aspect of the invention contains up to 95 wt % of compounds of formula IIA or IIB, up to 15 wt % of a compound formula III, and up to 25 wt % of a compound of formula I, the total being 100 wt %.

Liquid crystal materials of this aspect of the invention may be used in the known types of liquid crystal electro-optical display device.

Examples of the invention will now be described, referring to FIGS. 1, 2 and 3 which schematically show preparative routes to compounds of formula I. In each case the boronic acids were prepared using the methods described in the examples of PCT/EP88/00724. In each case all liquid crystal transition temperatures are in °C, eg K70 SA means solid crystal to SA liquid crystal at 70° C.

EXAMPLE 1

Route B (1) Preparation of

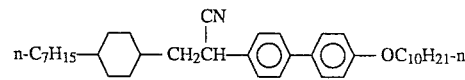

B1

1-(4-Bromophenyl)-1-cyano-2-(trans-4-heptylcyclohexyl)ethane

Lithiumdiisopropylamide (LDA) (1.5 in THF) (5.13 ml, 7.7 mmol) was added dropwise under dry nitrogen to a stirred and cooled (−70° C.) mixture of trans-4-heptylcyclohexylmethyl-toluene- 4-sulphonate (2.8 g, 7.7 mmol) and 4-bromophenylacetonitrile (1.37 g, 7.0 mmol) in sodium-dried tetrahydrofuran (10 ml) and molecular sieve-dried hexamethylphosphoramide (HMPA) (5 ml). The reaction mixture was stirred for 1 h at −70° C. and then allowed to warm to room temperature overnight and monitored by GC. The reaction mixture was poured onto water (50 ml) and the product was extracted into ether (2×20 ml). The combined extracts were washed with water and dried (MgSO$_4$). The solvent was removed under reduced pressure and the crude product was purified by column chromatography [silica gel; eluting with chloroform-light petroleum (bp 40°–60° C.)(1:2)]; yield 1.43 g, 52% mp 56°–57° C.

B2

1-Cyano-2-(4'-decyloxybiphenyl-4-yl)-1-(trans-4 -heptylcyclohexyl)ethane

A stirred mixture of the product of step A1 (2.64 mmol), 4-decyloxyphenylboronic acid (0.99 g, 3.43 mmol), tetrakis(triphenylphosphine)palladium(0) (0.4 g, 0.34 mmol), 2M sodium carbonate solution (3 ml), benzene (10 ml) and methanol (1 ml) was heated under reflux under dry nitrogen for 4 h and the reaction was monitored by GC. The reaction mixture was cooled and 2M sodium carbonate solution (100 ml) was added followed by aqueous ammonia (2 ml) and ether (100 ml). The organic layer was separated and the aqueous layer was washed with ether (50 ml). The combined ether extracts were washed with water and dried (MgSO₄). The solvent was removed under reduced pressure and the crude product was purified by column chromatography [silica gel; eluting with dichloromethane: light petroleum (bp 60°–80° C.)(3.1)]. Yield 62%, recrystallised from ethanol.

(2) Preparation of

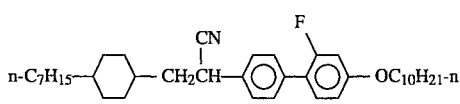

This was prepared by an analogous method to that of (1) above using the product of Step B1 and 4-decyloxy-2-fluorophenylboronic acid. Election was on silica gel using dichloromethane: light petroleum (bp 40°–60° C.)(1:5). Yield 64% recrystallised from ethanol.

EXAMPLE 2

Route A (1) Preparation of

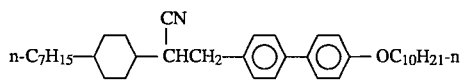

A1

1-(4-Bromophenyl)-2-cyano-2-(trans-4-heptylcyclohexyl)ethane

Was prepared similarly as step B1 of example 1 above from trans-4-heptylcyclohexylacetonitrile and 4-bromobensylbromide; yield 59%; mp 60°–62° C.

A2

1-Cyano-2-(4'-decoxybiphenyl-4-yl)-2-(trans-4 -heptylcyclohexyl)ethane

Was prepared similarly as for step B2 above using the product of step A1 and 4-decoxyphenylboronic acid. [silica gel; eluting with chloroform-light petroleum (bp 40°–60° C.) (1.5)]; yield 62% recrystallised from ethanol.

(2) Preparation of

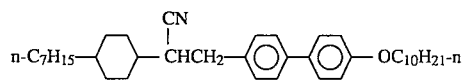

Was prepared similarly as A1–A2 above using 1-(4-bromophenyl)-2-cyano-2-(trans-4-heptylcyclohexyl)ethane and 4-decoxy-2-fluorophenylboronic acid. [Silica gel; eluting with dichloromethane-light petroleum (bp 40°–60° C.)(1:5)]; yield 36%; recrystallised from ethanol.

(3) Preparation of

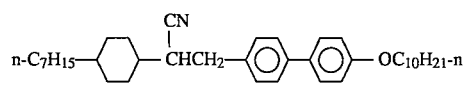

Was prepared similarly as A1–A2 above using 1-(4-bromophenyl)-2-cyano-2-(trans-4-heptylcyclohexyl)ethane and 4-decoxy-3-fluorophenylboronic acid. [Silica gel; eluting with dichloromethane-light petroleum (bp 40°–60° C.)(1:5)]; yield 27%; recrystallised from ethanol.

EXAMPLE 3

Preparation of

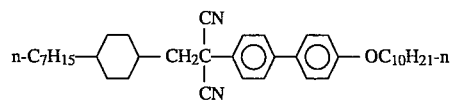

The Ketone 1-(4'-decyloxybiphenyl-4-yl)-2-(trans-4 -heptylcyclohexyl) ethanone was prepared using a method analogous to that used for the corresponding octyloxy compound in Mol. Cryst. Liq. Cryst (1988). An alternate route was that of example 1 of EP-A-0117631. The yield was 18%.

Another route to this Ketone used the reaction between 1-(4-bromophenyl)-2-(trans-4-heptylcyclohexyl)ethan-1-one (1.0 g, 2.64 mmol) and 4-decyloxyphenylboronic acid (0.99 g, 3.43 mmol) following a procedure analogous to that of B2 above. In the column chromatography stage silica gel was used and the eluent was dichloromethane: light petroleum (bp 40°–60° C. (1:1). Yield 0.85 g 61%, recrystallised from ethanol. The Ketone showed liquid crystal transitions K106 $S_G$ 135 Sc 142 $S_A$ 168 I.

To a solution of this Ketone (0.467 mmol) in molecular-sieve dried dichloromethane (5 ml) was added titanium tetrachloride (0.545 mmol, dropwise) at 0° C. under dry nitrogen. After 30 minutes trimethylsilylcyanide (TMS-CN) 0.934 mmol) was added at 0° C. and the mixture was stirred for 72 hours at room temperature.

The reaction mixture was poured into water and the crude product was extracted into dichloromethane (2×25 ml). The combined extracs were washed with water and dried (MgSO₄). The solvent was removed under reduced pressure and the crude product was purified by column chromatography [(silica gel, eluting with dichloromethane: light petroleum (bp 40°–60° C. (1:5)]. The product was recrystallised from ethanol. Yield 50%.

Using analogous routes the following Ketones were prepared:

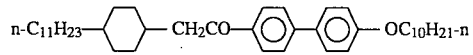

K 106 $S_G$ 135 $S_C$ 147 $S_A$ 160 I (eluent dichloromethane: light petroleum (40°–60° C.) 1:2, yield 26% recrystallised from ethanol).

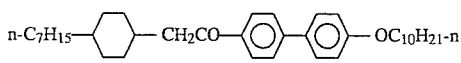

K 117 $S_G$ 132 $S_C$ 141 $S_A$ 163 I (eluent chloroform: light petroleum (40°–60° C.) 1:2, yield 10% recrystallised from ethanol).

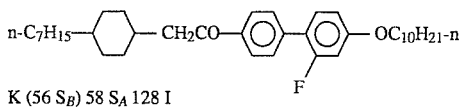

K (56 $S_B$) 58 $S_A$ 128 I (eluent dichloromethane: light petroleum (40°–60° C.) 4:1, yield 93% recrystallised from light petroleum (40°–60° C.).

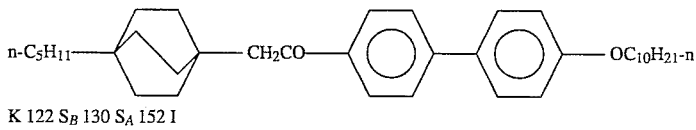

K 122 $S_B$ 130 $S_A$ 152 I (prepared from 1-pentylbicyclo (2,2,2) octane 4-acetic acid via the acyl chloride (via SOCl$_2$) and Mol. Cryst. Liq. Cryst (1988) route. Eluent chloroform: light petroleum (40°–60° C.) 1:2, yield 19%, recrystallised from light petroleum (40°–60° C.).

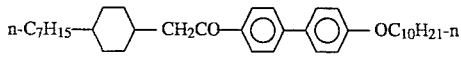

K (56 $S_B$) 68 $S_A$ 138 I was prepared by another route as follows:

The Grignard reagent of 4-bromo-4'decoxy-2-fluorobiphenyl (known) (6.1 g, 15 mmol), magnesium metal (0.4 g, 16.6 mg atom) in sodium-dried ether (25 ml) was prepared at 50° C. under anhydrous conditions and the reaction was monitored by GC. A solution of trans-4-heptylcyclohexylacetonitrile (1.1 g, 5 mmol) in sodium-dried ether (10 ml) was added and the reaction mixture was heated under reflux overnight. The reaction mixture was cooled and then poured onto ice (100 g) and 36% hydrochloric acid (10 ml). The organic layer was separated and the aqueous layer was washed with ether (25 ml). The combined ether extracts were washed with aqueous sodium carbonate (10%) (50 ml), water and then dried (MgSO$_4$). The solvent was removed under reduced pressure and the crude product was purified by column chromatography [silica gel; eluting with chloroform: light petroleum (bp 40°–60° C.) (1:2)]; yield 1.75 g, 64%; recrystallised from ethanol.

EXAMPLE 4

Preparation of

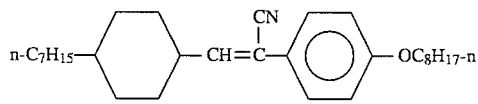

Titanium tetrachloride (55 µl, 0.545 mmol) was added dropwise to a solution of 2-(trans-4-heptylcyclohexyl)-1-(4-octoxyphenyl)ethanone (0.2 g, 0.467 mmol) in molecular sieve-dried dichloromethane (5 ml) at 0° C. under dry nitrogen. After 30 min, TMS-CN (0.142 ml, 0.934 mmol) was added at 0° C. and then the mixture was stirred for 72 h at room temperature. The reaction mixture was poured onto water and the crude product was extracted into dichloromethane (2×25 ml).

The combined extracts were washed with water and dried (MgSO$_4$). The solvent was removed under reduced pressure and the crude product was purified by column chromatography [silica gel; eluting with dichloromethane-light petroleum (bp 40°–60° C.) (1:2)]; yield 0.15 g, 68%; recrystallised from ethanol.

Liquid crystal transitions (in °C.) of the cyano compounds prepared in the above examples and by related methods are listed below:

TABLE 2 n-C$_7$H$_{15}$—[cyclohexyl]—CH(A)—C(B)(Z)—[phenyl]—[phenyl(X,Y)]—OC$_{10}$H$_{21}$-n

| A | B | Z | X | Y | K | $S_B$ | $S_C$ | $S_A$ | N | I |
|---|---|---|---|---|----|-------|-------|-------|-----|-----|
| CN | H | H | H | H | 86 | → | (75) → | 124 | | |
| H | CN | H | F | H | 70 | → | | (65) | | |
| CN | H | H | F | H | 52 → | (47) → | (67) → | 90 | | |
| CN | H | H | H | F | 89 | → | | 126 | | |
| H | CN | H | H | H | | | | 72 | → | 99 |

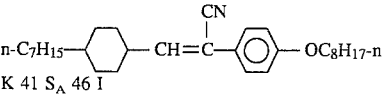

K 41 $S_A$ 46 I

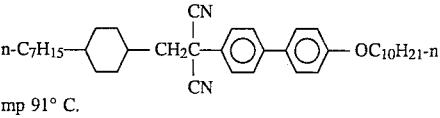

mp 91° C.

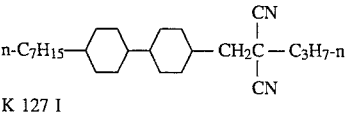

K 127 I

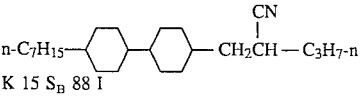

K 15 $S_B$ 88 I

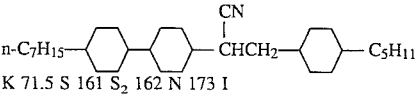

K 71.5 S 161 $S_2$ 162 N 173 I

TABLE 2-continued n-C₇H₁₅—◯—CH(A)—C(B)(Z)—◯(X,Y)—OC₁₀H₂₁-n n-C₇H₁₅—◯—CH(CN)CH₂—◯—C₅H₁₁-n
K 47 S$_A$ 66 I n-C₅H₁₁—◯—CH(CN)(CH₂)₄CH(CN)—◯—C₅H₁₁-n
K 106.5 I n-C₅H₁₁—◯—◯—CH₂CH₂CH(CN)CH₂—◯—C₅H₁₁
K 53 S$_B$ 70 I n-C₅H₁₁—◯—◯—CH₂CH₂C(CN)(CN)CH₂—◯—C₅H₁₁
K 104 (S$_B$ 93) I

EXAMPLE 5

A representative example of Route C.

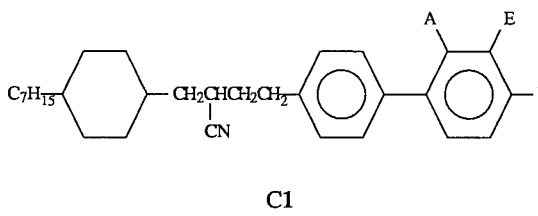

C1

A solution of trans-4-heptylcyclohexylcarboxylic acid (3) (10 g/0.044 mol) in thionyl chloride (75 ml) and DMF (3 drops) was heated with stirring under reflux for 3 hours. After cooling, the excess thionyl chloride was removed under vacuum. The residue was treated with dry ether (50 ml) and again concentrated under vacuum.

Dry ether (50 ml) was carefully added to lithium aluminium hydride (3.35 g/0.088 mol) under dry nitrogen). To this stirred suspension a solution of the crude acid chloride was added in dry ether (20–30 ml) over one hour at room temperature. The stirred suspension was heated under reflux for 2 hours and then cooled. Water (1.5 ml) was added to destroy excess LiAlH₄. The mixture was then quenched with dilute HCl (10%). The solution was extracted with ether (3×100 ml) and the combined organic extracts washed with water (3×50 ml), dried (MgSO₄) and the solvent removed under vacuum. The residue was purified by distillation at 125° C./0.1 mm Hg to give the product as a colourless oil. Yield 75%.

C2

To a stirred solution of alcohol (4) (10 g/0.047 mol) in alcohol free chloroform (47 ml) was added pyridine (7.6 ml/0.094 mol) at 0° C. To this mixture was added tosyl chloride (13.44 g/0.071 mol) in small portions. The mixture was stirred at 0° C. for 2 hours and then at room temperature for a further 2 hours. Ether (120 ml) and water (28 ml) were added. The organic layer was separated off and washed successively with dilute HCl, water 5% NaHCO₃ and water. After drying (MgSO₄) the solvent was removed under vacuum and the crude residue purified by flash-silica chromatography (2% diethyl ether in pet. ether 40/60). The product was a white solid. Yield 67%; m.pt. 33°–35° C.

C3

Finely powdered succinic anhydride (10 g/0.1 mol) was thoroughly mixed in a 250 ml flask with powdered AlCl₃ (27 g/0.2 mol). Bromobenzene (37.5 ml/0.36 mol) was added and the mixture stirred and heated at 100°–110° C. for one hour. Clouds of HCl were given off and the solid dissolved to give a dark red solution. The reaction mixture was cooled and then poured on to ice water containing conc. HCl (30 ml). The mixture was extracted with ethyl acetate (3×150 ml). The combined organic extracts were washed with aq. 2M NaOH (3×150 ml). The combined aqueous extracts were acidified using conc. HCl. The precipitated solid product was filtered off and dried at the pump. Recrystallisation from ethanol gave the crystalline acid. Yield 64%; m.pt. 141°–143° C.

C4

A mixture of mossy zinc (46 g), mercury (II) chloride (3.45 g), conc. HCl (2.3 ml) and water (57 ml) was stirred at room temperature for 5–10 minutes. The solution was decanted off and to the amalgamated zinc was added water (30 ml), conc. HCl (80 ml), glacial acetic acid (2 ml), toluene (40 ml) and β-(p-bromobenzoyl)propanoic acid (20 g/0.078 mol). The mixture was stirred and heated under reflux for 9 hours. After cooling, the organic layer was separated off, washed with water and dried (MgSO₄). After filtration the solvent was removed under vacuum and the residue distilled. The product was collected at 146° C./0.5 mmHg. Yield 55%.

C5

A solution of acid (7) (10 g/0.04 mol) in thionyl chloride (100 ml) containing DMF (a few drops) was stirred overnight at room temperature. The thionyl chloride was then removed under vacuum to give the crude acid chloride. The acid chloride was dissolved in diglyme (20 ml) and this solution was added slowly to stirred aqueous ammonia (35%, 200 ml). The resultant mixture was stirred for a further 30 minutes. The solid was filtered and washed with cold water. After drying (vacuum oven, 50° C.) a sample was recrystallised from pet. ether 40/60 and ethyl acetate. The bulk of the material was carried on to the next step without further purification. Yield 83%.

C6

To a stirred solution of amide (8) (7.0 g/0.029 mol) in dry DMF (170 ml) was added a solution of thionyl chloride (21/0.29 mol) in dry DMF (170 ml) dropwise at room temperature. It was then poured onto water (500 ml) and the product extracted with ether (3×100 ml). The combined organic extracts were washed with water, aqueous NaHCO₃ solution, water and then dried (MgSO₄). After removal of the solvent under vacuum the dark residue was distilled under vacuum. The product was collected at 150°–160° C./0.1 mm Hg. Yield 83%.

C7

To a stirred solution of di-isopropylamine (4.7 ml/0.035 mol) in dry THF (25 ml) under dry nitrogen at 0° C., was added n-BuLi (13.6 ml of 2.5 M solution/0.034 mol). After stirring for 30 minutes at 0° C., the temperature was lowered to −78° C. and nitrile (9) (6 g/0.027 mol) was added dropwise. The mixture was stirred for a further one hour at −78° C. A solution of tosylate (5) (10.1 g/0.027 mol) in dry THF (8 ml) was then added dropwise and the mixture stirred for one hour at −78° C. and then allowed to warm up to room temperature. After stirring overnight the reaction was quenched with aqueous $NH_4Cl$ solution and extracted with ether (3×50 ml). The combined organic extracts were washed with water and sat. brine and dried ($MgSO_4$). The solvent was removed under vacuum and the residue subjected to flash-silica chromatography (eluent 5% diethyl ether in pet. ether 40/60). The product was a crystalline solid. Yield 24%.

C8

A solution of 4-pentylphenylboronic acid (0.7 g/3.15 ml) was added to a stirred mixture of nitrile (10) 1 g/2.39 mmol) and tetrakis(triphenylphosphine) palladium (0) (0.15 g/0.13 mmol) in benzene (30 ml) and 2M $Na_2CO_3$ solution (30 ml) at room temperature and under dry nitrogen. The stirred mixture was heated under reflux and the reaction monitored by TLC. Once complete, the mixture was cooled and diluted with some ether and some water. The mixture was extracted with ether (3×50 ml). The combined organic extracts were washed with brine and dried ($MgSO_4$). The solvent was removed under vacuum and the residue purified by flash-silica chromatography (eluent 40% dichloromethane in pet. ether 40/60). The solid product was recrystallised from hexane. Yield 83%. The product prepared using 4-pentylphenylboronic acid was 1-(trans-4-Heptylcyclohexyl)-2-cyano-4-(4-pentylbiphenyl-4'-yl)butane (compound 1a of Table 3).

The following compounds were similarly prepared using different boronic acids:

1-(trans-4-Heptylcyclohexyl)-2-cyano-4-(4-hexoxybiphenyl-4'-yl)butane (compound 1b of Table 3); purification by flash-silica chromatography (eluent 40% dichloromethane in pet. ether 40/60) followed by recrystallisation from hexane/ethyl acetate. Yield 97%.

1-(trans-4-Heptylcyclohexyl)-2-cyano-4-(4-octoxybiphenyl-4'-yl)butane (compound 1c of Table 3); purification by flash-silica chromatography (eluent 30% dichloromethane in pet. ether 40/60) followed by recrystallisation from pet. ether 40/60. Yield 26%.

1-(trans-4-Heptylcyclohexyl)-2-cyano-4-(4-decoxybiphenyl-4'-yl)butane (compound 1d of Table 3); purification by flash-silica chromatography (eluent 30% dichloromethane in pet. ether 40/60) followed by recrystallisation from pet. ether 40/60. Yield 33%.

1-(trans-4-Heptylcyclohexyl)-2-cyano-4-(2-fluoro-4-octoxybiphenyl-4'-yl)butane (compound 1e of Table 3); purification by flash-silica chromatography (eluent 30% dichloromethane in pet. ether 40/60) followed by recrystallisation from pet. ether 40/60. Yield 20%.

1-(trans-4-Heptylcyclohexyl)-2-cyano-4-(2,3-difluoro-4-octoxybiphenyl-4'-yl)butane (compound 1f of Table 3); purification by flash-silica chromatography (eluent 30% dichloromethane in pet. ether 40/60) followed by recrystallisation from ethanol. Yield 33%.

Table 3 shows a list of the derivatives prepared and their respective transition temperatures.

TABLE 3

| | Transition Temperatures of Compounds 1a–f | | | |
|---|---|---|---|---|
| Compound | Y | A | E | Transition Temperatures/°C. |
| 1a | —$C_5H_{11}$ | H | H | K 86.5 $S_A$ 93.0 I |
| 1b | —$OC_6H_{13}$ | H | H | K 116.0 ($S_A$ 105.5) I |
| 1c | —$OC_8H_{17}$ | H | H | K 115.8 $S_A$ 116.9 I |
| 1d | —$OC_{10}H_{21}$ | H | H | K 109.5 $S_A$ 113.6 I |
| 1e | —$OC_8H_{17}$ | F | H | K 63.0 $S_A$ 76.0 I |
| 1f | —$OC_8H_{17}$ | F | F | K 46.7 $S_A$ 61.5 I |

EXAMPLE 6

A representative example of Route D.

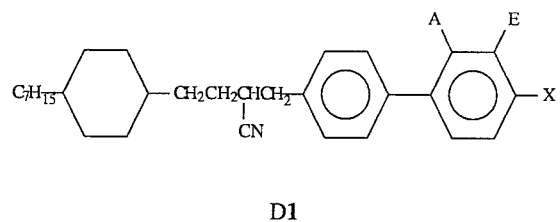

D1

This method followed that used in step C1. The product was purified by distillation, b.pt. 140°–150° C./0.25 mmHg. Yield 70%.

D2

This method followed that used in step C2. The product was purified by flash-silica chromatography (eluent 2% diethyl ether in pet. ether 40/60). Yield 92%.

D3

A stirred solution of p-bromobenzaldehyde (10 g/0.05 mol) and malonic acid (11.44 g/0.11 mol) in pyridine (25 ml) containing piperdine (0.4 ml) was heated at 100°–110° C. for 3 hours. After cooling, the solution was poured onto water (200 ml) containing conc. HCl (25 ml) with stirring. The precipitated product was filtered, washed with water and dried. The product was recrystallised from ethanol, m.pt. 254°–256° C. Yield 98%.

D4

The method followed that used in step C5. The product was purified by crystallisation from ethyl acetate/ethanol, m.pt. 206°–209° C. Yield 97%.

D5

A solution of amide (16) (7.6 g/0.034 mol) in ethanol/THF (200 ml) containing $PtO_2$ catalyst (0.2 g) was stirred under hydrogen until the uptake of the gas had ceased. The catalyst was filtered off and the solvent removed under vacuum. The product was purified by recrystallisation from ethyl acetate, m.pt. 138°–138° C. Yield 95%.

D6

The method followed that used in step C6. The product was purified by distillation, b.pt. 135° C./0.1 mm Hg. Yield 83%.

D7

The method followed that used in step C7. The product was purified by flash-silica chromatography (eluent 5% diethyl ether in pet. ether 40/60). Yield 54%.

D8

The method followed that used in step C8. The product was purified by flash-silica chromatography (eluent 30% dichloromethane in pet. ether 40/60) followed by recrystallsation from hexane. Yield 91%. The compound prepared using 4-pentylphenylboronic acid was 1-(4-trans-Heptylcyclohexyl)-3-cyano-4-(4-pentylbiphenyl- 4'-yl)butane (compound 2a of Table 4).

The following systems were similarly prepared using different boronic acids.

1-(4-trans-Heptylcyclohexyl)-3-cyano-4-(4-hexoxybiphenyl- 4'-yl)butane (compound 2b of Table 4); purification by flash-silica chromatography (eluent 40% dichloromethane in pet. ether 40/60) followed by recrystallisation from ethyl acetate/pet. ether 40/60; yield 87%.

1-(4-trans-4-Heptylcyclohexyl)-3-cyano-4-(4-octoxybiphenyl- 4'-yl)-butane (compound 2c of Table 4); purification by flash-silica chromatography (eluent 30% dichloromethane in pet. ether 40/60 followed by recrystallisation from ethanol/ethyl acetate. Yield 98%.

1-(4-trans-4-Heptylcyclohexyl)-3-cyano-4-(4-decoxybiphenyl- 4'-yl)-butane (compound 2d of Table 4); purification by flash-silica chromatography (eluent 35% dichloromethane in pet. ether 40/60) followed by recrystallisation from ethanol/ethyl acetate. Yield 73%.

1-(4-trans-Heptylcyclohexyl)-3-cyano-4-(2-fluoro-4 -octoxybiphenyl-4'-yl)butane (compound 2e of Table 4); purification by flash-silica chromatography (eluent 35% dichloromethane in pet. ether 40/60 followed by recrystallisation from ethanol/ethyl acetate. Yield 66%.

1-(4-trans-Heptylcyclohexyl)-3-cyano-4-(2,3-difluoro-4 -octoxybiphenyl-4'-yl)butane (compound 2f of Table 4); purification by flash-silica chromatography (eluent 35% dichloromethane in pet. ether 40/60 followed by recrystallisation from ethanol/ethyl acetate or acetone. Yield 58%.

Table 4 shows a list of the derivatives prepared and their respective transition temperatures.

TABLE 4

Transition Temperatures of Compounds 2a–f

| Compound | X | A | E | Transition Temperatures/°C. |
|---|---|---|---|---|
| 2a | $-C_5H_{11}$ | H | H | K 98.0 ($S_A$ 91.7) I |
| 2b | $-OC_6H_{13}$ | H | H | K 113.5 $S_A$ 119.5 I |
| 2c | $-OC_8H_{17}$ | H | H | K 110.0 $S_A$ 116.4 I |
| 2d | $-OC_{10}H_{21}$ | H | H | K 106.3 $S_A$ 113.8 I |
| 2e | $-OC_8H_{17}$ | F | H | K 72.9 $S_C$ 81 $S_A$ 86 I |
| 2f | $-OC_8H_{17}$ | F | F | K 92.2 $S_A$ 94.5 I |

EXAMPLE 7

A representative Example of Route G
Preparation of

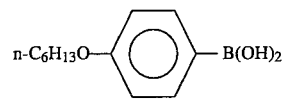

G1

A solution of 1-bromohexane (60 g) in acetone (150 ml) was added dropwise to a stirred mixture of 4-bromophenol (71 g) and $K_2CO_3$ (120 g) in acetone (600 ml) at room temperature. The stirred mixture was heated under reflux for 43 hr (i.e. until glc revealed complete reaction). The product was extracted into ether twice, and the combined ethereal extracts were washed with water, 5% NaOH. water and dried ($MgSO_4$). The solvent was removed in vacuo and the residue was distilled (bp=100°–110° C. at 0.1 mm Hg) to yield a colourless liquid (79.4 g, 86%).

G2

A solution of the Grignard Reagent prepared from G1 (72 g) and Mg (7.75 g) in dry THF (250 ml) was added dropwise to a stirred, cooled (–78° C.) solution of tri-isopropyl borate (109.1 g) in dry THF (40 ml) under dry $N_2$. The stirred mixture was allowed to warm to room temperature overnight and stirred with 10% HCl (320 ml) at room temperature for 1 hr. The product was extracted into ether twice, and the combined ethereal extracts were washed with water and dried ($MgSO_4$). Solvent was removed in vacuo to yield a colourless solid (61.2 g, 99%) mp=80°–85° C.

An example of the use of a compound of Formula I in a liquid crystal material and device embodying the present invention will now be described with reference to FIG. 6.

Figure 6:
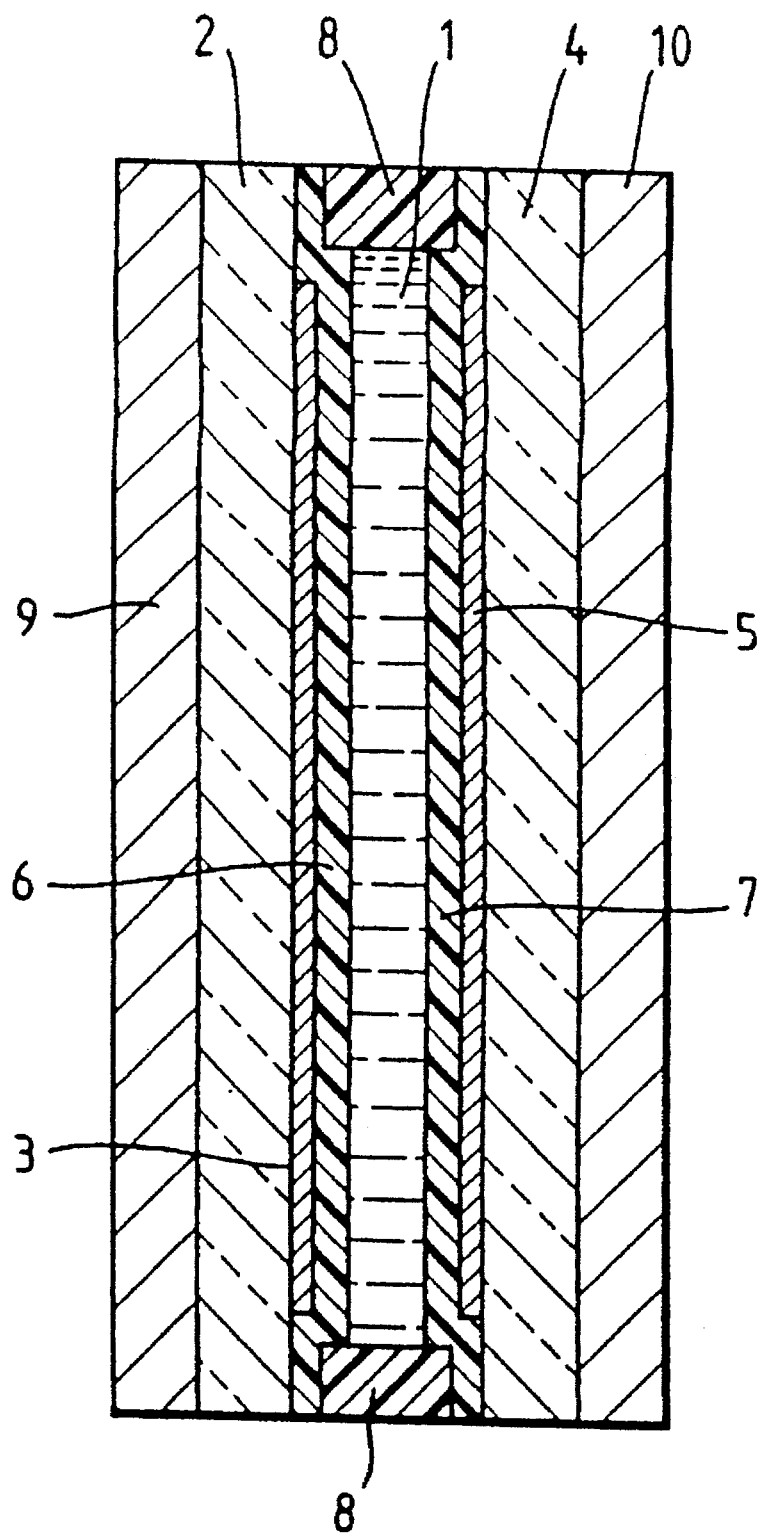
FIG. 6 is a cross-sectioned representation of a liquid crystal cell.

In FIG. 6, a liquid crystal cell comprises a layer 1 of liquid crystal material exhibiting a chiral smectic phase sandwiched between a glass slide 2 having a transparent conducting layer 3 on its surface, e.g. of tin oxide or indium oxide, and a glass slide 4 having a transparent conducting layer 5 on its surface. The slides 2, 4 bearing the layers 3,5 are respectively coated by films 6,7 of a polyimide polymer. Prior to construction of the cell the films 6 and 7 are rubbed with a soft tissue in a given direction, the rubbing directions being arranged parallel upon construction of the cell. The spacer 8 e.g. of polymethyl methacrylate, separates the slides 2,4 to the required distance, e.g. 5 microns.

The liquid crystal material 1 is introduced between the slides 2, 4 by filling the space between the slides 2, 4 and spacer 8 and sealing the spacer 8 in a vacuum in a known way. Preferably the liquid crystal material is in the smectic A, nematic or isotropic liquid phase (obtained by heating the material) when is introduced between the slides 2, 4 to facilitate alignment of the liquid crystal molecules with the rubbing directions on the slides 2, 4.

A polarizer 9 is arranged with its polarization axis parallel to the rubbing direction on the films 6, 7 and an analyzer (crossed polarizer) 10 is arranged with its polarization axis perpendicular to that rubbing direction.

When a square wave voltage (from a conventional source not shown) varying between about +10 volts and –10 volts is applied across the cell by making contact with the layers 3 and 5 the cell is rapidly switched upon the change in sign of the voltage between a dark state and a light state as explained above.

In an alternative device (not shown) based on the cell construction shown in FIG. 6 the layers 3 and 5 may be selectively shaped in a known way, e.g. by photoetching or deposition through a mask, e.g. to provide one or more display symbols, e.g. letters, numerals, words or graphics and the like as conventionally seen on displays. The electrode portions formed thereby may be addressed in a variety of ways which include multiplexed operation.

The liquid crystal material 1 may be any one of the mixtures described in the preceding examples.

We claim:

1. A cyanoalkane of the formula I which shows liquid crystalline properties:

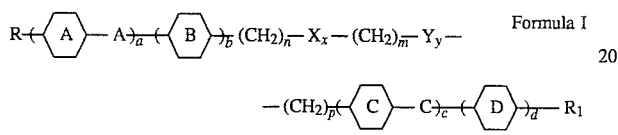

wherein R and R$^1$ are independently C$_{1-12}$ alkyl, alkoxy, perfluoroalkyl or perfluoroalkoxy;

rings A, B, C and D are independently phenyl, which may carry one or two halogen substituents, trans-cyclohexyl, or (2,2,2) bicyclooctyl, each of a, b, c or d being independently 0 or 1 provided (a+b+c+d) is 2 or 3;

links A and C are independently a single bond, CH$_2$CH$_2$, COO, OOC, CH$_2$O or OCH$_2$;

n, m and p are independently 0 or an integer 1 to 4 provided (n+m+p) is not 0;

X and Y are independently selected from —CHCN— and —C(CN)$_2$—;

x, y are 0 or 1, provided that at least one of x, y is 1;

provided that when groups of formula CH$_2$O or C(CN)(H) are bonded directly via their C atoms to any cycloaliphatic moiety then at least one of the rings A, B, C, D carries at least one fluorine; and when groups of formula CH$_2$O or C(CN)(H)CH$_2$ are bonded directly via their CH$_2$ atoms to any aromatic moiety then at least one of the rings A, B, C, D carries at least one fluorine.

2. A cyanoalkane according to claim 1 wherein R and R$^1$ are n-alkyl or n-alkoxy or asymmetrically substituted alkyl or alkoxy.

3. A cyanoalkane according to claim 1, wherein rings A and B are cyclohexyl.

4. A cyanoalkane according to claim 1, wherein if rings C and D are halogen substituted phenyl the halogen is fluorine.

5. A cyanoalkane according to claim 1, wherein the links A and C are single bonds.

6. A cyanoalkane according to claim 1, wherein if c and d are O, R$^1$ is alkyl.

7. A cyanoalkane according to claim 1, wherein only ring A is (2,2,2,) bicyclooctyl.

8. A cyanoalkane according to claim 1, wherein n, y and p=0; x, m=1 and X=CHCN.

9. A cyanoalkane according to claim 1, wherein m, y and p=0, n, x=1 and X=CHCN.

10. A cyanoalkane according to claim 1, wherein m, y, p=0; n, x=1, X=C(CN)$_2$.

11. A cyanoalkane according to claim 1, wherein y, p=0; x, m=1; n= 2; X=CHCN or C(CN)$_2$.

12. A cyanoalkane according to claim 1, wherein n, p=0; x, y=1; m= 4; X, Y=CHCN.

13. A cyanoalkane according to claim 1, having the formula IA4, IA5, IB2, IB3 or IB4:

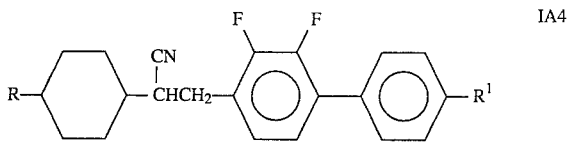

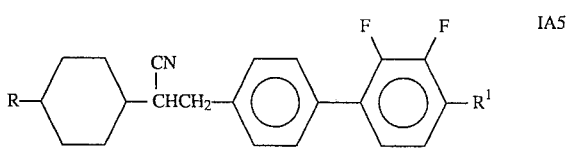

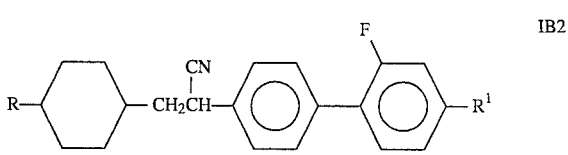

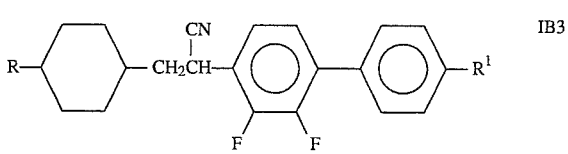

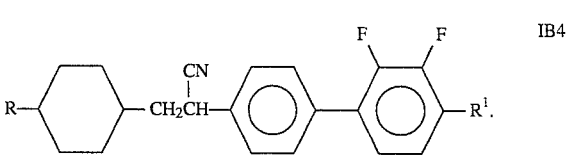

14. A liquid crystal material being a mixture of compounds including at least one compound as claimed in claim 1.

15. A liquid crystal material according to claim 14, wherein the mixture additionally contains at least one compound of formula IIA:

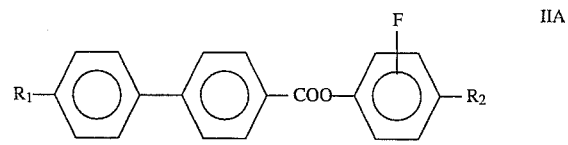

wherein R$_1$ and R$_2$ are independently C$_2$–C$_{12}$ alkyl or alkoxy.

16. A liquid crystal material according to claim 14, wherein the mixture additionally contains at least one compound of formula IIB1, formula IIB2 or formula IIB3:

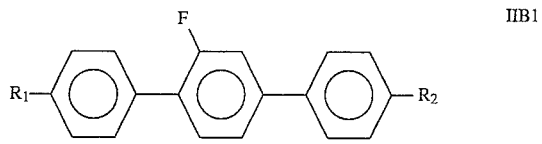

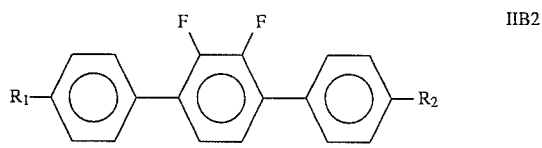

-continued

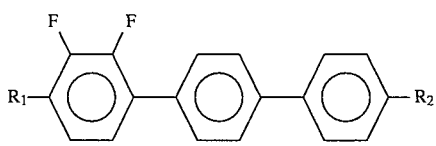
IIB3 wherein $R_1$ and $R_2$ are independently $C_2$–$C_{12}$ alkyl or alkoxy.

17. A liquid crystal material according to claim 14, 15 or 16 wherein the mixture additionally contains at least one compound of formula III:

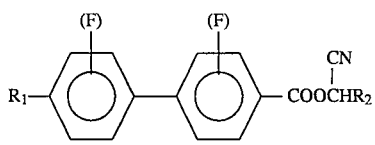
III wherein $R_1$ may be $C_{1-12}$ n-alkyl or n-alkoxy; $R_2$ may be $C_{1-15}$ alkyl including n-alkyl, a branched chain and optically active alkyl; and (F) indicates that the rings may carry a lateral fluorine substituent.

18. A liquid crystal material according to claim 14 in which the mixture contains up to 95 wt. % of compounds of formula IIA

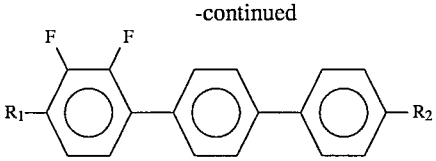
IIB3 wherein $R_1$ and $R_2$ are independently $C_2$–$C_{12}$ alkyl or alkoxy;

up to 15% of a compound of formula III

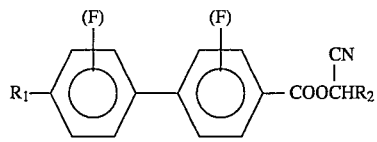
III wherein $R_1$ may be $C_{1-12}$ n-alkyl or n-alkoxy; $R_2$ may be $C_{1-15}$ alkyl including n-alkyl, a branched chain and optically active alkyl; and (F) indicates that the rings may carry a lateral fluorine substituent;

and up to 25 wt. % of a compound of formula I, the total being 100 wt. %.

19. A liquid crystal electrooptical display device including a liquid crystal material as claimed in claim 14.

20. A ferroelectric smectic liquid crystal material being a mixture of compounds wherein at least one of the said compounds is a compound having the Formula I:

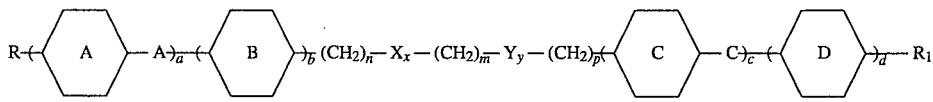

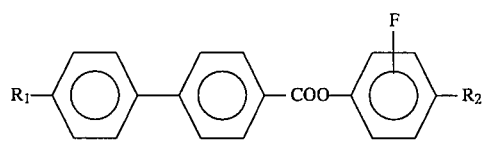
IIA wherein $R_1$ and $R_2$ are independently $C_2$–$C_{12}$ alkyl or alkoxy;

or compounds of IIB1, IIB2 or IIB3

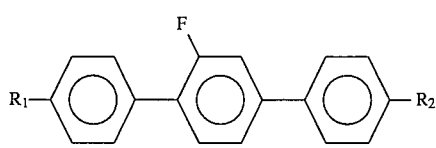
IIB1

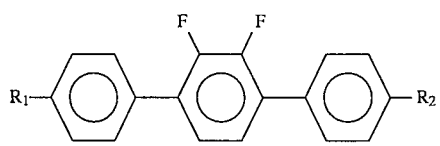
IIB2 wherein R and $R_1$ independently $C_1$–$C_{12}$ alkyl, alkoxy, perfluoroalkyl or perfluoroalkoxy; rings A, B, C and D are independently phenyl, which may carry one or two halogen substituents, trans-cyclohexyl, or (2,2,2) bicyclooctyl, each of a, b, c or d being independently 0 or 1 provided (a+b+c+d) is 2 or 3;

links A and C are independently a single bond, $CH_2CH_2$, COO, OOC, $CH_2O$ or $OCH_2$;

n, m and p are independently 0 or an integer 1 to 4 provided (n+m+p) is not 0;

X and Y are independently selected from —CHCN and —C(CN)$_2$;

x and y are 0 or 1, provided that at least one of x and y is 1;

provided that: when a+b+c+d=3, whichever of

are present are all trans cyclohexyl, x+y=1, R and $R_1$ are both selected from alkyl, n+m+p=1, A and C are both single bonds, then whichever of X or Y is present is C(CN)$_2$;

provided that: when a+b+c+d=3, whichever of

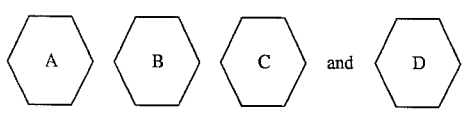

are present are chosen from trans cyclohexyl and phenyl, are not all the same, x+y=1, R and $R_1$ are both selected from alkyl, and n+m+p=1, whichever of A and C are present are selected from COO and single bond provided that at least one of A or C is COO, then whichever of X or Y is present is $C(CN)_2$.

21. A ferroelectric smectic liquid crystal material according to claim 20, wherein R and $R_1$ are n-alkyl or n-alkoxy or asymmetrically substituted alkyl or alkoxy.

22. A ferroelectric smectic liquid crystal material according to claim 20, wherein rings A and B are cyclohexyl.

23. A ferroelectric smectic liquid crystal material according to claim 20, wherein if rings C and D are halogen substituted phenyl the halogen is fluorine.

24. A ferroelectric smectic liquid crystal material according to claim 20 wherein the links A and C are single bonds.

25. A ferroelectric smectic liquid crystal material according to claim 20, wherein if c and d are 0, $R_1$ is alkyl.

26. A ferroelectric smectic liquid crystal material according to claim 20 wherein only ring A is (2,2,2) bicyclooctyl.

27. A ferroelectric smectic liquid crystal material according to claim 20 wherein n, y and p=0; x, m=1 and X=CHCN.

28. A ferroelectric smectic liquid crystal material according to claim 20, wherein m, y and p=0; n, x=1 and X=CHCN.

29. A ferroelectric smectic liquid crystal material according to claim 20, wherein m, y, p=0; n, x=1, $X=C(CN)_2$.

30. A ferroelectric smectic liquid crystal material according to claim 20, wherein y, p=0; x, m=1; n=2; X=CHCN or $C(CN)_2$.

31. A ferroelectric smectic liquid crystal material according to claim 20, wherein n, p=0; x, y=1; m=4; X, Y=CHCN.

32. A ferroelectric smectic liquid crystal material according to claim 20, wherein the compound of formula I is a compound given by the formula IA1, IA4, IA5, IB2, IB3, or IB4:

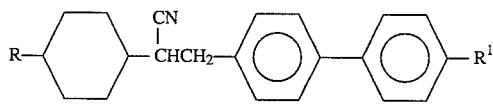

IA1

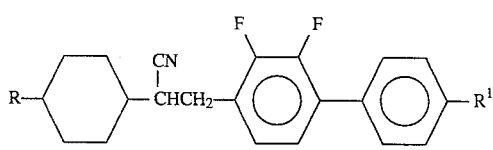

IA4

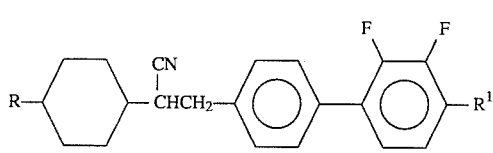

IA5

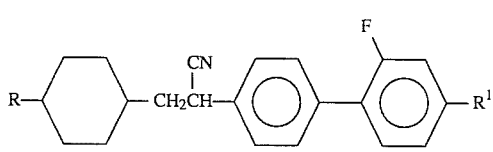

IB2

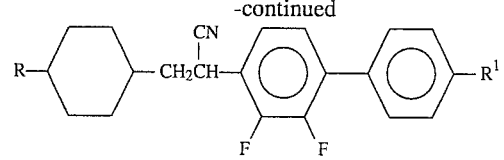

IB3

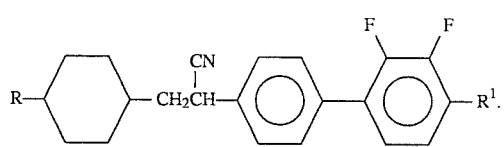

IB4

33. A ferroelectric smectic liquid crystal material according to claim 20, wherein the mixture additionally contains at least one compound of formula IIA:

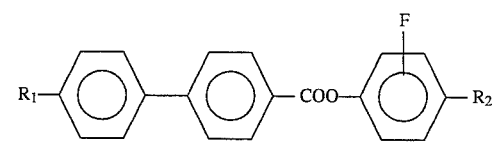

IIA wherein $R_1$ and $R_2$ are independently $C_2$–$C_{12}$ alkyl or alkoxy.

34. A ferroelectric smectic liquid crystal material according to claim 20, wherein the mixture additionally contains at least one compound of formula IIB 1, formula IIB2 or formula IIB3:

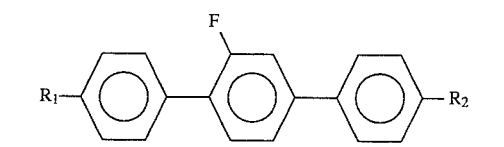

IIB1

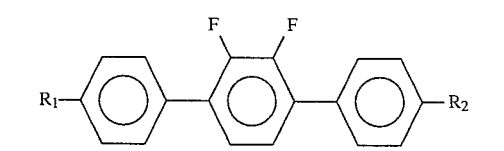

IIB2

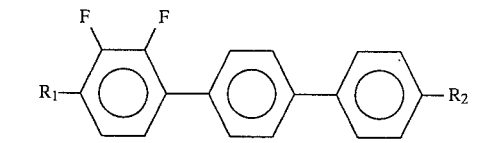

IIB3 wherein $R_1$ and $R_2$ are independently $C_{2-12}$ alkyl or alkoxy.

35. A ferroelectric smectic liquid crystal material according to claim 20, 33 or 34 wherein the mixture contains at least one compound of Formula III:

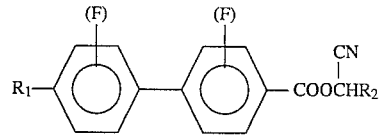

III wherein $R_1$ may be $C_{1-12}$ n-alkyl or n-alkoxy and $R_2$ may be $C_{1-15}$ alkyl, including n-alkyl, branched alkyl and optically active alkyl, (F) indicates that the rings indicated may carry a lateral fluorine substituent.

36. A liquid crystal electrooptical display device incorporating a mixture of liquid crystals as claimed in claim 20.

* * * * *